ROSE PLANT
Filed Jan. 5, 1973 2 Sheets-Sheet 1
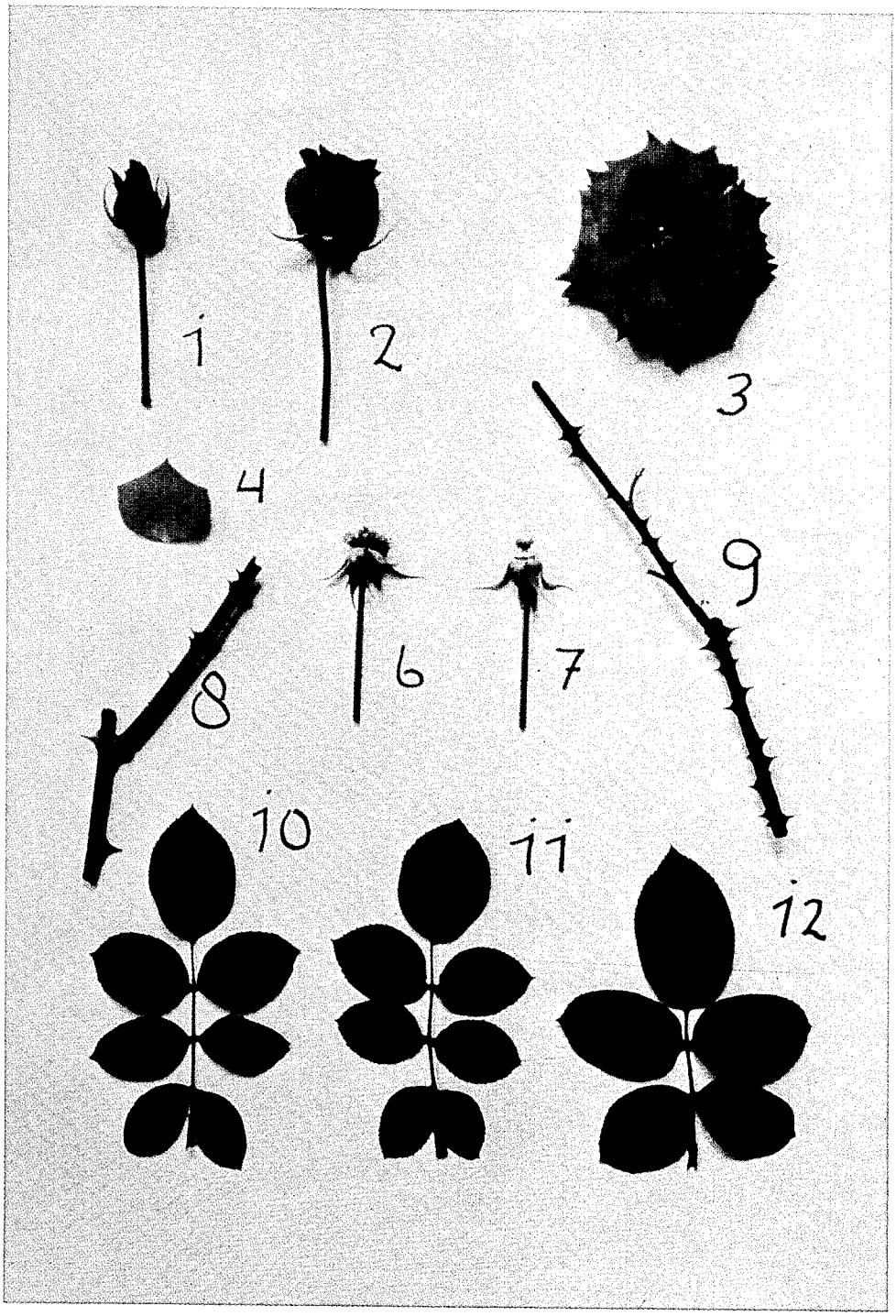

United States Patent Office

Plant Pat. 3,540

Patented Apr. 9, 1974

3,540

ROSE PLANT

Gijsbert Verbeek, Hornweg 109, Aalsmeer, Netherlands

Filed Jan. 5, 1973, Ser. No. 321,374
Claims priority, application Belgium, Sept. 22, 1972, 122,319
Int. Cl. A01h 5/00
U.S. Cl. Plt.—20 1 Claim

ABSTRACT OF THE DISCLOSURE

A rose plant of the hybrid tea class, particularly for the greenhouse, originated by crossing an unnamed and unpatented seedling of Romantica × Edith Piaf with the variety known as Miracle (Plant Pat. No. 1,863).

SUMMARY OF THE INVENTION

The present invention relates to a new and distinct variety of rose plant of the hybrid tea class, which was originated by me by crossing an unnamed and unpatented seedling of Romantica × Edith Piaf with the variety known as Miracle (Plant Patent No. 1,863), the former being the seed parent and the latter being the pollen parent.

As the result of this breeding, I have produced a new and improved rose variety having the following unique combination of characteristics which are outstanding therein and which distinguish it from its parents, as well as from all other varieties of which I am aware:

(1) A tall and upright, very vigorous habit of growth, with cutting stems of good length when grown under greenhouse conditions.
(2) Leaves with a leathery substance and good resistance to mildew.
(3) A more or less continuous production of flowers when grown under greenhouse conditions.
(4) Long flower stems.
(5) A perfect shape of flower and a size ranging from medium to large.
(6) Good flower petalage.
(7) A high-centered flower form with long lasting qualities of flowers and long retention of the perfect form after opening.
(8) A distinctive and attractive shape of the buds substantially as described and illustrated.
(9) A distinct and attractive flower color ranging between Orient Red and Geranium Lake.

In comparison with its pollen parent Miracle, the new variety rarely produces more than a single flower to a stem, whereas the flowers of the pollen parent are borne in groups.

In comparison with its unnamed seed parent, the new variety has the same upright habit of growth, but the flowers have greater petalage and have substantially greater substance and lasting qualities; the flower color may be generally described as Orient Red instead of the Currant Red of the seed parent.

Asexual reproduction of my new variety by budding and grafting, as performed at Aalsmeer, Netherlands, shows that the aforementioned characteristics and distinctions come true to form and are established and transmitted through succeeding propagations.

BRIEF DESCRIPTION OF THE DRAWINGS

The accompanying drawings show typical specimens of the vegetative growth and flowers of my new variety in different stages of development and as depicted in color as nearly true as it is reasonably possible to make the same in color illustrations of this character, and wherein:

FIG. 1 shows the bud of the flower when just opening the sepals;
FIG. 2 shows the flower when opening the first petals;
FIG. 3 shows the flower when completely opened;
FIG. 4 shows one of the petals;
FIG. 6 shows a receptacle and showing the stamens;
FIG. 7 shows a receptacle showing the pistils after removing the stamens;
FIG. 8 shows one of the main branches;
FIG. 9 shows one of the branches that is ramified;
FIG. 10 shows one of the leaves with a composition of seven leaflets showing the upper surface;
FIG. 11 shows one of the leaves with a composition of seven leaflets showing the under surface;
and
FIG. 12 shows one of the leaves with a composition of five leaflets showing the upper surface.

DETAILED DESCRIPTION OF DISCLOSURE

Figure 5:
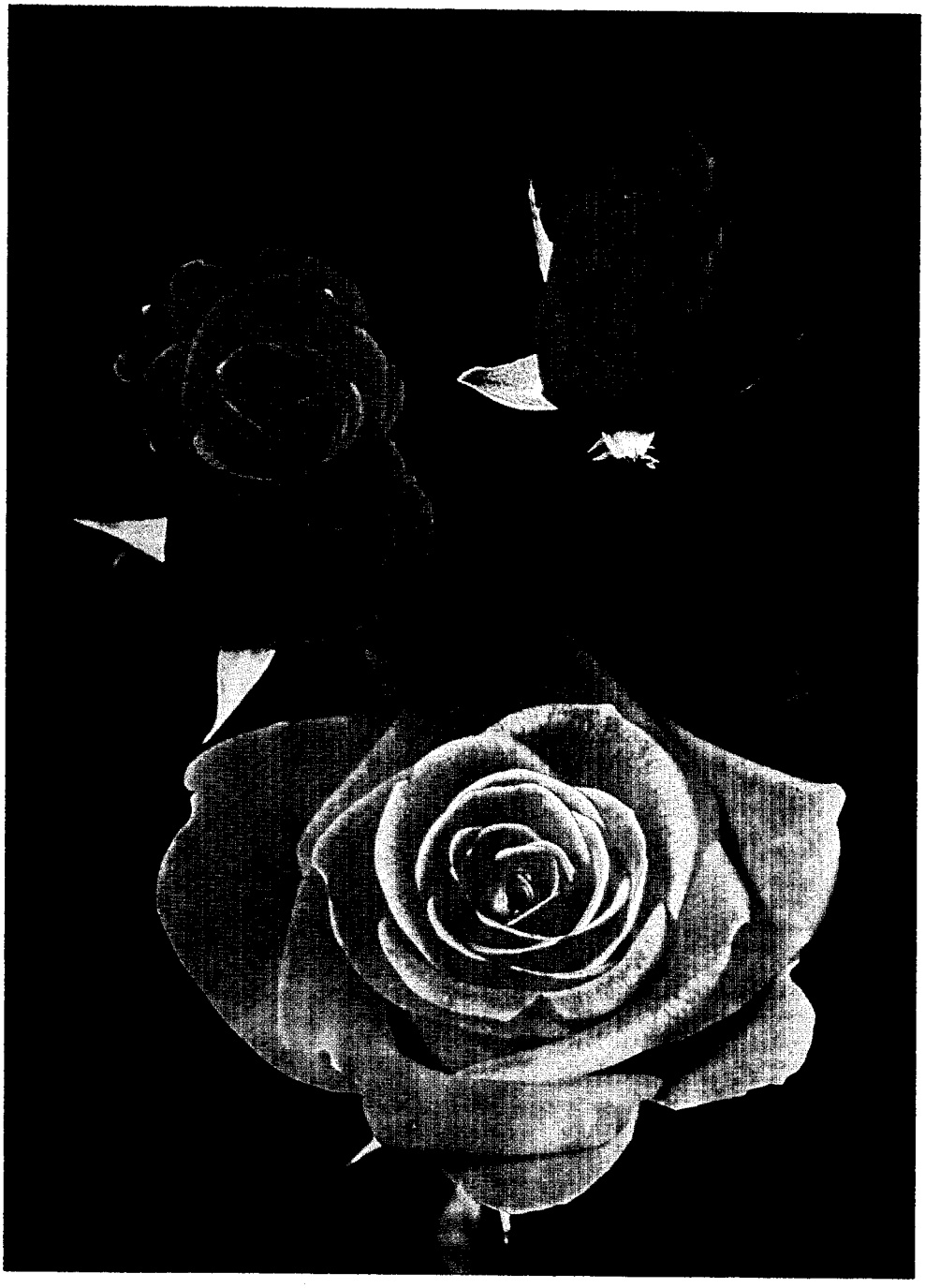
FIG. 5 is a view of the flower in different stages of development.

The following is a detailed description of my new variety, with color terminology in accordance with the "Wilson Colour Chart" I and II, published by the British Colour Council, except where general color terms of ordinary dictionary significance are obvious:

*Essential information*

Type: Hardy, bush; greenhouse; seedling; for cut flowers.
Class: Hybrid tea.
Breeding: Seedling.
*Seed parent.*—Unnamed and unpatented seedling of Romantica × Edith Piaf.
*Pollen parent.*—Miracle (Plant Pat. No. 1,863).
Propagation: Holds its distinguishing characteristics through succeeding propagations by budding and grafting.

*Flower*

Locality where grown: Aalsmeer, Netherlands.
Flowers borne: Singly to stem; on strong long stems.
Quantity of blood: Abundant in greenhouse.
Continuity: Continuous during growing season.
Fragrance: Very slight.
Bud:
*Peduncle.*—Average length; average caliper, erect; smooth except for some stiff glands and few prickles. Color: Lettuce Green (HCC 861/1).
*Before calyx breaks.*—Size: Medium. Form: Medium length, ovoid, without foliacous appendage on the surface of the bud.
*As calyx breaks.*—Color: Blood Red (HCC 820/1).
*Sepals.*—Inner surface: With fine wooly tomentum. Margins: With gland-tipped cilia.
*As first petals open.*—Size: Average. Form: Medium length, ovoid.
*Color.*—Outside: Turkey Red (HCC 721/2). Inside: Dutch Vermilion (HCC 717). Opening: It does open up very well.
Bloom:
*Size.*—When fully open—large, 4 inches to 4½ inches.
*Petalage.*—Double from 38 to 42 petals, arranged regularly.
*Form.*—High to medium centered; petals remaining at first somewhat cupped; becoming later at maturity cupped with tips rolled outward.
Petals:
*Texture.*—Thick, moderately leathery; with inside slightly satiny.
*Shape.*—Outside—broader than long, with apex rounded. Intermediate—broadly ovate, with apex rounded. Inside—nearly round, with apex rounded.

This description of a newly opened flower was made from a rose grown in a greenhouse in July 1972 at Aalsmeer, Netherlands:

Color:

*Outer petal.*—Outside surface—Cherry (HCC 722); towards base—Cherry (HCC 722/2); inside surface—Geranium Lake (HCC 20);

*Intermediate petal.*—Outside surface: Cherry (HCC 722); inside surface: Blood Red (HCC 820).

*Inner petal.*—Outside surface: Turkey red (HCC 721/1); inside surface: Orient Red (HCC 819/1) (719).

This description was made from a rose that was open for three days in a greenhouse in July 1972 at Aalsmeer, Netherlands:

Color:

*Outer petal.*—Outside surface: Turkey Red (HCC 721/2); inside surface: Geranium Lake (HCC 20).

*Intermediate petal.*—Outside surface: Carmine (HCC 21); towards base: Claret Rose (HCC 021); inside surface: Blood Red (HCC 820).

*Inner petal.*—Outside surface: Turkey Red (HCC 721/2); inside surface: Orient Red (HCC 819/1).

General color effect:

*Newly opened flower.*—Orient red (HCC 819).

*Three days open.*—Blood Red (HCC 820).

Behavior: Drops off cleanly.

Flower longevity: Cut roses, grown in greenhouse and kept at living room temperature—8 days in July.

*Reproductive organs*

Stamens: From medium to many, arranged regularly about pistils and mixed a few with petaloids;

*Number.*—Average: 150 to 170.

*Filaments.*—Medium length; all with anthers.

*Color.*—Cherry (HCC 722/2).

*Anthers.*—Medium size, all open at once approximately; color, upper side: Buttercup Yellow (HCC 5/2); color, under side: Egyptian Buff (HCC 407).

*Pollen.*—Moderate quantity. Color: Buttercup Yellow (HCC 5).

*Pistils.*—Many: 100 to 110.

*Styles.*—Average caliper; separated. Color: Currant Red (HCC 821/1).

*Stigma.*—Color—Majolica Yellow (HCC 09/2).

*Plant*

Foliage:

*Leaves.*—Compound, usually of 5–7 leaflets; moderately abundant; medium to large size; leathery, medium thickness; glossy.

Leaflets:

*Shape.*—Ovoid.

*Apex.*—Acute.

*Base.*—Round.

*Margin.*—Generally simply serrate.

*Color.*—Mature—upper surface: Spinach Green (HC 0960/1); under surface: Lavender Green (HCC 000761/1). Young—upper surface: reddish green with veins and margins reddish purple; under surface: reddish green.

Rachis (the supporting stem of the compound leaf): average size:

*Upper side.*—Grooved; lined with moderate quantity of stipitate glands.

*Under side.*—Sparsely prickly; occasionally with 1 or 2 prickles.

Stipules: From short to medium length; narrow; with medium length points turning out at an angle of about 45°.

Disease: Good resistance to powdery mildew and blackspot, as determined by comparison with many other varieties grown under comparable conditions at Aalsmeer, Netherlands.

Growth:

*Habit.*—Tall, bushy, upright, much branched.

*Growth.*—Vigorous.

*Canes.*—Medium to heaxy caliper.

Main stems:

*Color.*—Fern Green (HCC 0862).

*Large prickles.*—Medium large; several; medium length; straight; with short elliptical base; color: Brown.

*Small prickles.*—Color—brown.

*Hairs.*—None.

Branches:

*Color.*—Moderately bright green.

*Large prickles.*—Several; medium length; straight; with short, elliptical base; color: Brown.

*Small prickles.*—Few; color: Brown.

*Hairs.*—None.

New shoots:

*Color.*—Reddish purple.

*Large prickles.*—Few to medium; medium length, straight; with short elliptical base; color: Reddish purple with pale green tips.

*Small prickles.*—From none to very few; color: Reddish purple.

*Hairs.*—None.

I claim:

1. A new and distinct variety of rose plant of the hybrid tea class, substantially as herein shown and described, characterized particularly as to novelty by the unique combination of a vigorous and bushy habit of growth with leaves of a leathery and very glossy substance with good mildew and blackspot resistance, suitable for greenhouse culture for commercial cut flowers, with long stems, many flowers for year-round culture with good flower petalage, good form of the flowers, long lasting qualities of the flowers both on the plant and when cut, and a distinctive and attractive general color tonalty of the flowers ranging between Orient red and Geranium Lake.

No references cited.

ROBERT E. BAGWILL, Primary Examiner